United States Patent [19]

Blum

[11] Patent Number: 4,469,906

[45] Date of Patent: Sep. 4, 1984

[54] PROCESS FOR STABILIZING EPOXIDE-CONTAINING PERCHLOROETHYLENE

[75] Inventor: Klaus Blum, Burghausen, Fed. Rep. of Germany

[73] Assignee: Wacker-Chemie GmbH, Munich, Fed. Rep. of Germany

[21] Appl. No.: 528,453

[22] Filed: Sep. 1, 1983

[30] Foreign Application Priority Data

Dec. 17, 1982 [DE] Fed. Rep. of Germany ....... 3246886

[51] Int. Cl.$^3$ .............................................. C07C 21/12
[52] U.S. Cl. .................................................... 570/116
[58] Field of Search ......................................... 570/116

[56] References Cited

U.S. PATENT DOCUMENTS 4,217,310  8/1980  Cormany ............................ 570/116

Primary Examiner—Charles F. Warren
Assistant Examiner—Joseph A. Boska
Attorney, Agent, or Firm—Collard, Roe & Galgano

[57] ABSTRACT

A process for the stabilization of perchloroethylene which contains known epoxides as stabilizing agents which is characterized by addition of an effective amount of 1,2-epoxycyclooctane and/or 1,2-5,6-diepoxycyclooctane. As a result of this addition the cleaning effect of the perchloroethylene on metals is maintained for longer periods, corrosion phenomena are avoided and formation of greasy deposits on the goods to be cleaned will no longer take place.

2 Claims, No Drawings

PROCESS FOR STABILIZING EPOXIDE-CONTAINING PERCHLOROETHYLENE

The invention relates to a process for stabilizing perchloroethylene containing as a stabilizing agent known epoxides.

It is known to use, particularly for the purposes of degreasing metals, highly stabilized perchloroethylene, which contains in addition to antioxidants, acid-binding agents from the group of epoxides. These epoxides are, however, liable to undergoing regrouping or rearranging reactions, which are catalyzed by the Lewis acids ever present in traces in the perchloroethylene in use; such Lewis acids are zinc chloride, iron chloride, aluminum chloride and others. From the regrouping reactions, products will result which have no stabilizing action. The inherent accelerated degradation of the epoxide, consequently, destabilizes the perchloroethylene in use.

A typical example for an epoxide used for the stabilization of perchloroethylene, is cyclohexene oxide. Cyclohexene oxide is rearranged to cyclopentyl aldehyde which has no stabilizing effect. From DE-OS 28 53 848 it has become known that the rearrangement can be suppressed with 2,3-epoxypropanol, but, unfortunately, 2,3-epoxypropanol tends to cause polycondensation reactions resulting in products which form greasy deposits on the material to be cleaned and on the walls of the cleaning apparatus.

It is therefore the object of the present invention to stabilize epoxide-containing perchloroethylene.

More particularly, it is an object of the invention to prevent, or at least decrease, the rearrangement of the epoxides taking place under the influence of Lewis acids.

According to the invention, these objects are achieved by the addition of 1,2-epoxycyclooctane and/or 1,2-5,6-diepoxycyclooctane to perchloroethylene stabilized with epoxides.

The invention therefore consists in a process for the stabilization of perchloroethylene which contains known epoxides, and is characterized by adding an effective amount of 1,2-epoxycyclooctane and/or 1,2-5,6-diepoxycyclooctane. These amounts are 0.5 to 10% by weight, and especially 1–4% by weight, calculated on the amount of the other epoxides present.

1,2-Epoxycyclooctane and 1,2-5,6-diepoxycyclooctane are known commercial products. They are, for instance, obtained by epoxidation reactions of cyclooctene or cyclooctadiene, respectively.

In practical application, the choice of epoxides known as acid-binding agents is mostly made with the fact in mind that their boiling points do not differ by more than 15° C. from the boiling point of stabilized perchloroethylene. Typical examples of such epoxides are epoxybutane, 1,2-epoxyhexane and its isomers, 1,2-epoxyoctane and its isomers, diisobutylene oxide, cyclohexene oxide and 5,6-epoxyhexene-1.

As a rule, the mentioned epoxides are used in amounts of 1,000 to 5,000 ppm. by weight, especially in amounts of 2,000 to 3,000 ppm. by weight, calculated on the total weight of stabilized perchloroethylene.

Accordingly, in the preferred method of carrying out the process, an amount of 50 to 500 ppm. by weight, especially 80 to 150 ppm. by weight of 1,2-epoxycyclooctane and/or 1,2-5,6-diepoxycyclooctane are used calculated on the total weight of perchloroethylene to be stabilized. The addition of the epoxides according to the invention is made in the same manner as the addition of those previously added to the perchloroethylene to be stabilized.

The perchloroethylene stabilized according to the invention may also contain such stabilizing agents as were used up to now. These are especially amines, e.g., triethylamine, di-iso-propylamine, dimethylisobutylamine, sec.-butylamine, pentylamine, iso-pentylamine, 5-methyl-2-hexane-amine, di-iso-butylamine, N-methylpyrrole, N-methylmorpholine, and others.

Ethers, especially dialkyl ether, e.g., dibutyl ether, and di-sec.-butyl ether, dialkoxymethanes, e.g., dimethoxymethane and diethoxyethane, glycoldialkyl ether, e.g., dimethoxyethane, diethoxyethane and butylglycol-tert.-butyl ether, polyglycol ether, e.g., ethyl, diglycol-tert.-butyl ether, methoxydiglycol-tert.-butyl ether, triglycoldimethyl ether, aryl ether, e.g., diphenyl ether, aralkyl ether, e.g., dibenzyl ether, arylalkyl ether, e.g., anisole, hydrochinondimethyl ether.

Olefins, e.g., di-iso-butylene and cycloheptatriene.

Alkylphenols, e.g., p-cresol, o-cresol, 2,6-dimethylphenol, 2,4,6-trimethylphenol, p-iso-propylphenol, p-tert.-butylphenol, 2,6-di-tert.-butylphenol, p-amylphenol.

In the perchloroethylene made according to the invention, an epoxide combination is present, in which de-stabilizing rearrangement reactions of epoxides are suppressed substantially, even in the presence of Lewis' acids. Thus, it is surprisingly possible by adding small amounts of further epoxide to maintain the acid-binding of perchloroethylene in use for longer periods to avoid damage by corrosion, and prevent the formation of deposits on the storage containers as well as on the goods to be cleaned.

The invention will now be more fully described in a number of examples and comparison examples, but it should be understood that these are given by illustration only and not by limitation.

EXAMPLE 1

To perchloroethylene containing
100 ppm by weight of 1,2-5,6-diepoxycyclooctane
2,500 ppm by weight of 1,2-epoxycyclohexane
15 ppm by weight of di-isopropylamine
25 ppm by weight of 2,4-di-tert.-butylphenol
50 ppm by weight of N-methylmorpholine
200 ppm by weight anhydrous zinc chloride were added and boiled under reflux for 72 hours. The acid-binding capacity was measured by the capacity of adding hydrochloric acid according to the following method:

A solution of hydrochloric acid in isopropanol (4.4 cc conc. hydrochloric acid replenished to 500 cc with isopropanol) served as hydrochlorination agent. The titer of the solution was found by using 0.1 N NaOH with bromophenol Blue. (Consumption A) Then, 25 cc hydrochlorination agent, 10 cc of the above-described perchloroethylene, and 25 cc isopropanol were shaken and allowed to stand for 10 minutes at room temperature. Thereafter, back-titration was carried out with 0.1 N NaOH against bromophenol Blue (Consumption B).

The acid-binding capacity was calculated by the following formula:

$$\frac{(A - B) \times 4.0 \times 100 \times F}{V \times D \times 1000} = \% \text{ NaOH}$$

4.0 = effectiveness of 0.1 N NaOH in mg/cc
F = factor of 0.1 N NaOH
V = volume of perchloroethylene used in cc
D = density of the perchloroethylene in g/cc Result: The acid-binding capacity was 0.093% by weight NaOH.

COMPARISON EXAMPLE 1

The method of Example 1 was repeated with the difference that an otherwise equally stabilized perchloroethylene was used without added 1,2-5,6-diepoxycyclooctane.

Result: The acid-binding capacity was 0% by weight NaOH.

EXAMPLE 2

The method of Example 1 was repeated with the difference that instead of 2,500 ppm by weight of 1,2-epoxycyclohexane, 2,500 ppm by weight of a 4:1 mixture of 2,3-epoxyhexane and 3,4-epoxyhexane was used.

The stabilized perchloroethylene had an acid-binding capacity of 0.083% by weight NaOH.

COMPARISON EXAMPLE 2

The method of Example 2 was repeated with the difference that the addition of 100 ppm by weight of 1,2-5,6-diepoxycyclooctane was omitted.

Result: The acid-binding capacity was 0% by weight of NaOH.

EXAMPLE 3

The method of Example 1 was repeated with the difference that instead of 1,2-epoxycyclohexane, 2,500 ppm by weight of epoxyhexane was used.

Result: The acid-binding capacity was 0.078% by weight NaOH.

COMPARISON EXAMPLE 3

The method of Example 3 was repeated with the difference that the addition of 100 ppm by weight of 1,2-5,6-diepoxycyclooctane was omitted.

Result: The acid-binding capacity was 0% by weight of NaOH.

EXAMPLE 4

The method of Example 1 was repeated, with the difference that, instead of 100 ppm by weight of 1,2-5,6-diepoxycyclooctane, 100 ppm of 1,2-epoxycyclooctane were used.

Result: The acid-binding capacity was 0.078% by weight NaOH.

EXAMPLE 5

Specimens of stabilized perchloroethylene were introduced into a three-neck flask of 400 ml capacity provided with a reflux cooler, in which metal strips of copper, brass, zinc, aluminum and steel were so arranged that one half of the strips were immersed in the liquid. The material was refluxed for 168 hours.

The metal strips were then evaluated for corrosion and deposit formation. Furthermore, specimens of perchloroethylene treated as described above, were admixed with equal amounts of volume of water, violently shaken, and the pH value of the aqueous phase was finally determined.

Results: In the perchloroethylene described in Example 1, a pH value of 7.7 was found. The metal strips showed no corrosion.

In the perchloroethylene as described in Example 2, the pH value was 8.3. No corrosion.

In the perchloroethylene as described in Example 3, pH value was 8.3. No corrosion.

COMPARISON EXAMPLE 4

The method as in Example 5 with specimens of perchloroethylene was repeated, as described in Comparison Examples 1, 2 and 3.

In the specimen of perchloroethylene according to Comparison Example 1, all metal strips had a sticky deposit and showed signs of beginning corrosion. The pH was 4.2.

In the specimen according to Comparison Example 2, all metal strips shows signs of beginning corrosion, both the parts of the strips immersed and those extending above the liquid. The pH was 4.3. In the specimen according to Comparison Example 3, all metal strips showed signs of beginning corrosion, except the metal strips of zinc and aluminum. These showed no signs of corrosion in the parts extending above the liquid. The pH was 5.1.

Thus, while only several examples have been described, it is obvious that many changes and modifications may be made thereunto without departing from the spirit and scope of the invention.

What is claimed is:

1. A process for stabilizing perchloroethylene, which contains known epoxides as stabilizing agents, comprising the step of adding to said perchloroethylene an effective amount of a member of the group consisting of 1,2-epoxycyclooctane, 1,2-5,6-diepoxycyclooctane, and a mixture of both compounds.

2. The process of claim 1, wherein the amount of the members of the group is between 0.5 to 10% by weight, calculated on the amount of the known epoxides present.